United States Patent [19]

Rumberger et al.

[11] Patent Number: 5,663,642
[45] Date of Patent: Sep. 2, 1997

[54] RESONANT INDUCTIVE DEBRIS DETECTOR

[75] Inventors: William E. Rumberger, Newtown Square; Charles R. Gross, Norwood, both of Pa.

[73] Assignee: The Boeing Company, Seattle, Wash.

[21] Appl. No.: 607,107

[22] Filed: Feb. 26, 1996

Related U.S. Application Data

[63] Continuation-in-part of Ser. No. 764,303, Sep. 24, 1991, abandoned, and a continuation of Ser. No. 21,272, Feb. 22, 1993, Pat. No. 5,528,138.

[51] Int. Cl.$^6$ .................. G01N 27/74; G01R 33/12; G08B 17/10
[52] U.S. Cl. ............ 324/204; 324/236; 340/631
[58] Field of Search .................. 324/204, 226, 324/234, 236, 262; 340/631; 73/10, 861.08, 861.11, 53.05, 61.42

[56] References Cited

U.S. PATENT DOCUMENTS

| | | | |
|---|---|---|---|
| 2,162,009 | 6/1939 | Goldsmith | 175/183 |
| 2,683,030 | 7/1954 | Caule | 265/70 |
| 2,768,684 | 10/1956 | Castel et al. | 164/0.5 |
| 2,772,393 | 11/1956 | Davis | 324/40 |
| 2,902,765 | 9/1959 | Chater | 33/125 |
| 3,142,984 | 8/1964 | Harmon et al. | 73/194 |
| 3,883,796 | 5/1975 | Holt | 324/34 |
| 4,176,545 | 12/1979 | Oddo | 73/64 |
| 4,731,578 | 3/1988 | Tsaprazis | 324/204 |
| 4,831,362 | 5/1989 | Tsaprazis | 340/515 |
| 4,837,511 | 6/1989 | Whittington | 324/236 |
| 5,027,065 | 6/1991 | Bares | 324/204 |
| 5,041,856 | 8/1991 | Veronesi | 314/204 |
| 5,118,410 | 6/1992 | Rumberger | 210/85 |

*Primary Examiner*—Walter E. Snow
*Attorney, Agent, or Firm*—Jones, Tullar & Cooper, P.C.

[57] ABSTRACT

Apparatus is disclosed for detecting the presence of the type of debris in a fluid system. The apparatus detects the presence of debris, measures the accumulation and identifies the specific types of the debris. A plurality of sensors, connected in a bridge detecting circuit, are assembled in the apparatus in the fluid flow, each of said sensors are tuned to a specific preselected frequency which is characteristic of one material type of the debris. A variable frequency power supply is connected to the detecting bridge for exciting the bridge. Switching means are provided external to the detecting apparatus for selecting one of said sensors as the detecting leg of the bridge. When the sensor has been selected, the bridge is excited at the resonant frequency of the selected sensor for identifying a specific material type of the debris.

24 Claims, 6 Drawing Sheets

RESONANT INDUCTIVE DEBRIS DETECTOR

CROSS REFERENCE TO RELATED APPLICATIONS

This application is a continuation in part of applications Ser. No. 07/764,303, filed on Sep. 24, 1991, now abandoned and Ser. No. 08/021,272, filed Feb. 22, 1993, now U.S. Pat. No. 5,528,138 and also contains subject matter common to U.S. Pat. No. 5,118,410 issued Jun. 2, 1992 assigned to the assignee of this invention.

This invention relates in general to an electrical sensing apparatus for sensing the presence of and for measuring the incremental changes in the amount of debris in a fluid. More specifically, the present invention relates to an electrical resonant inductive apparatus for indicating the rate of accumulation of debris in a fluid as well as identifying the specific material types comprising the debris.

BACKGROUND OF THE INVENTION

Fluid systems used in mechanical devices for lubricating purposes or for transmitting power, become contaminated with debris comprising wear particles from the mechanical components of the device during the operational life of the machine. Such particles are derived from wear in bearings, gears and other components subject to frictional forces and from components that may have fractured due to excessive stress or imperfections in the manufacture of such components. The debris may comprise ferrous metals or non-ferrous metals as well as non-metallic compositions such as ceramic compounds. The detection of the presence of such debris, the rate of accumulation of the debris as well as the total amount of such debris, has been used to determine the degree of wear occurring in the device and also to predict impending failure by sensing the presence of large amounts of debris in the system. One such apparatus is described in U.S. patent application Ser. No. 07/764,303 and others are described in U.S. Pat. No. 5,118,410 which is referenced above, and also in U.S. Pat. No. 3,878,103 and U.S. Pat. No. 3,686,926. This application also describes a similar apparatus for detecting the presence of debris in the system and measuring the amount of debris present. These devices all contain a screen for trapping large particles present in the fluid and incorporate with the screen, a method of detecting the presence of debris particles. In the issued patents cited, debris is detected when an electrically conductive particle comes in contact with the metallic screen and completes the electrical circuit connected to the wire mesh of the screen. In the U.S. patent application cited above, there is disclosed an apparatus for using the inductive properties of a coil embedded in the screen to measure the amount of debris accumulated. In the two U.S. patents cited, the presence of large amounts of debris is sensed, but progressive, incremental accumulation and the total amount of debris cannot be suitably measured. Thus, the sensor often fails to accurately indicate an impending failure of the system and cannot indicate a rate of accumulation which would forecast the impending failure. U.S. patent application Ser. No. 07/764,303 cited above will measure debris accumulation and accumulation rate but the sensitivity of the device is limited.

SUMMARY OF THE INVENTION

The present invention overcomes the disadvantages of the prior art by providing a relatively simple device with high sensitivity which produces a high level, useful signal indicating the presence of incremental amounts of debris, the rate of accumulation and, more importantly, this invention will identify specific types of debris which enhances the condition monitoring capability of the device. Knowing material types, provides traceability to specific components within the apparatus thus providing a more comprehensive diagnosis of the condition of the system. Such features are of particular importance when the monitored apparatus is part of a helicopter drive system. Sudden failure of the drive system of a helicopter rotor can result in catastrophic failure of the system which most likely will lead to a crash of the aircraft. This apparatus, like the one disclosed in the patent application cited above, utilizes a screen member for collecting large particles and also contains electrical sensors for detecting the presence of debris in the system, however, this system also identifies the specific material types in the debris. The primary debris sensors are provided as inductive coil devices having relatively high resonant frequencies whose inductance changes with the presence of debris in the system. The high sensitivity of the device is achieved by tuning the inductive coils at or near their resonant frequency by adding conventional tuning components to the inductive sensor circuit. The sensors are electrically connected as one leg of a conventional bridge circuit. The bridge is excited with a voltage at the resonant frequency of the sensor coils. A second sensor is placed in the fluid stream to provide temperature compensation for the bridge circuit necessary because of the various temperatures involved in the operation of many fluid systems. It has been determined that each material type in the debris is best sensed when the sensor is excited at a particular preselected frequency which is characteristic of that material type to be sensed. By providing means for selectively changing the resonant frequency of the sensing coil and simultaneously changing the frequency of the bridge excitation voltage to the new sensor resonant frequency, the device can identify specific material types in the debris.

DETAILED DESCRIPTION OF THE INVENTION

Figure 1:
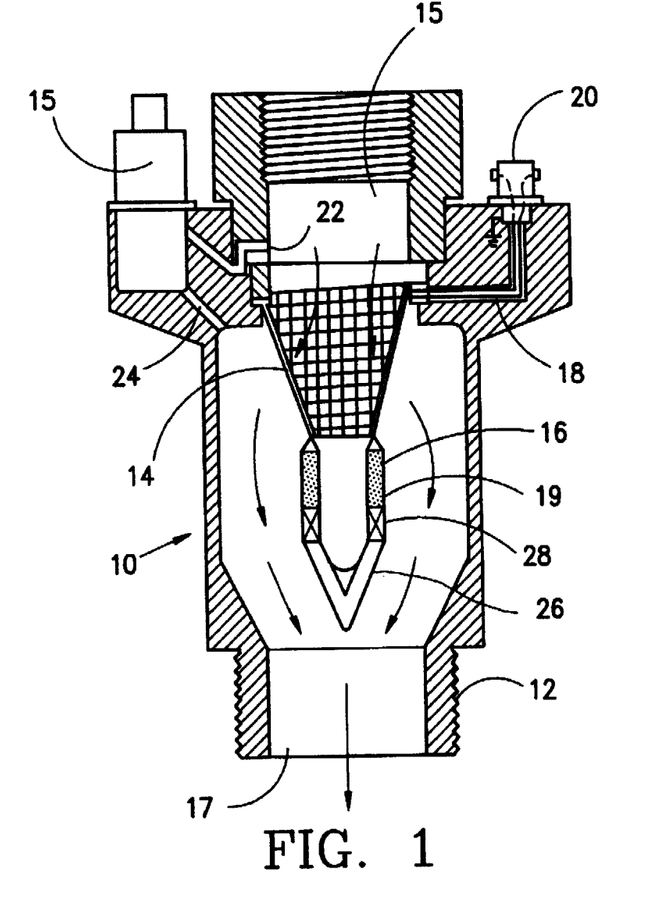
FIG. 1 is a sectional view of a typical device utilizing the invention.

FIG. 1 shows a resonant inductive sensing apparatus 10 according to the present invention. The inductive sensing apparatus 10 comprises a metal housing 12, open at both ends providing an inlet opening 15 and an outlet opening 17 to allow fluid, such as hydraulic, lubricating, or cooling fluid, to flow through the housing in the direction indicated by the arrows. The screen 14 is formed in a conical shape and fluid flowing into the inlet opening 15 escapes through the sides of the screen 14. The lower portion of the screen 14 is formed in a cylindrical shape and sensors 16 and 19 are placed to surround the cylindrical proportion. In this embodiment, the sensor 16 is the primary sensor and the sensor 19 is the compensating sensor providing temperature compensation to the bridge in order to adjust the output of the bridge due to changes in the fluid temperature. The sensors may be of several types which will be described in detail in connection with the discussion of FIGS. 4–7 below. The electrical connections from the sensors 16 and 19 are passed through the housing by means of conduit 18 to a terminal 20 at the top of the housing.

There is also provided a pressure differential sensor 15 which senses the pressure differential between the input and the output of the device by means of conduits 22 and 24. The output of the pressure sensor is an additional output signal which is activated if the housing becomes filled with debris. If the housing fills with debris, the differential pressure between the conduits 22 and 24 will rise rapidly and provide an additional indication of a large amount of debris in the system. The lower portion of the conical screen assembly 26 may be formed as a solid wall or may be formed of screen material. In order to trap additional ferrous material a permanent magnet 28 may be applied below the sensing coil 16.

Figure 2:
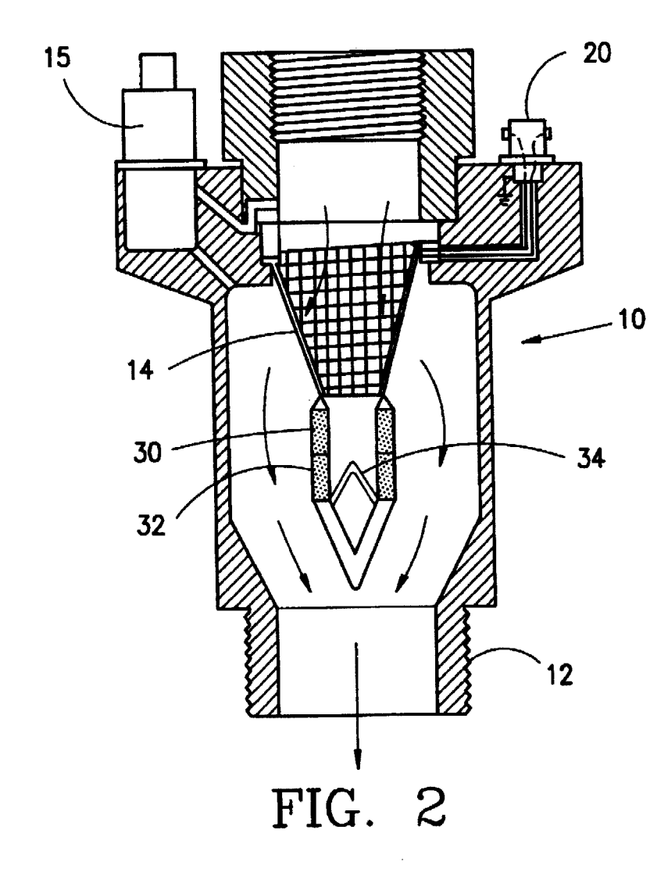
FIG. 2 is a sectional view of an alternate embodiment of the device.

Referring now to FIG. 2, there is shown an alternate embodiment of the invention. In this embodiment, the primary sensing coil 16 and the referenced sensor 19 have been replaced by two tuned inductive coil sensors 30 and 32 assembled one on top of the other about the cylindrical portion of the screen 14. An inverted conical member 34 has been inserted at the bottom of the cylindrical portion of the screen such that its apex is at the junction of the two sensors on the screen. Sensor 32 is the primary sensing coil and sensor 30 is the temperature compensating sensor for the bridge. The conical member 34 causes the accumulated debris to be gathered at the sensing coil 32 thus increasing the sensitivity of the device. If the total particle accumulation reaches the lower edge of coil 30, this sensor will also cause a change in the signal output of the bridge which will alert the user to high debris accumulation.

Figure 3:
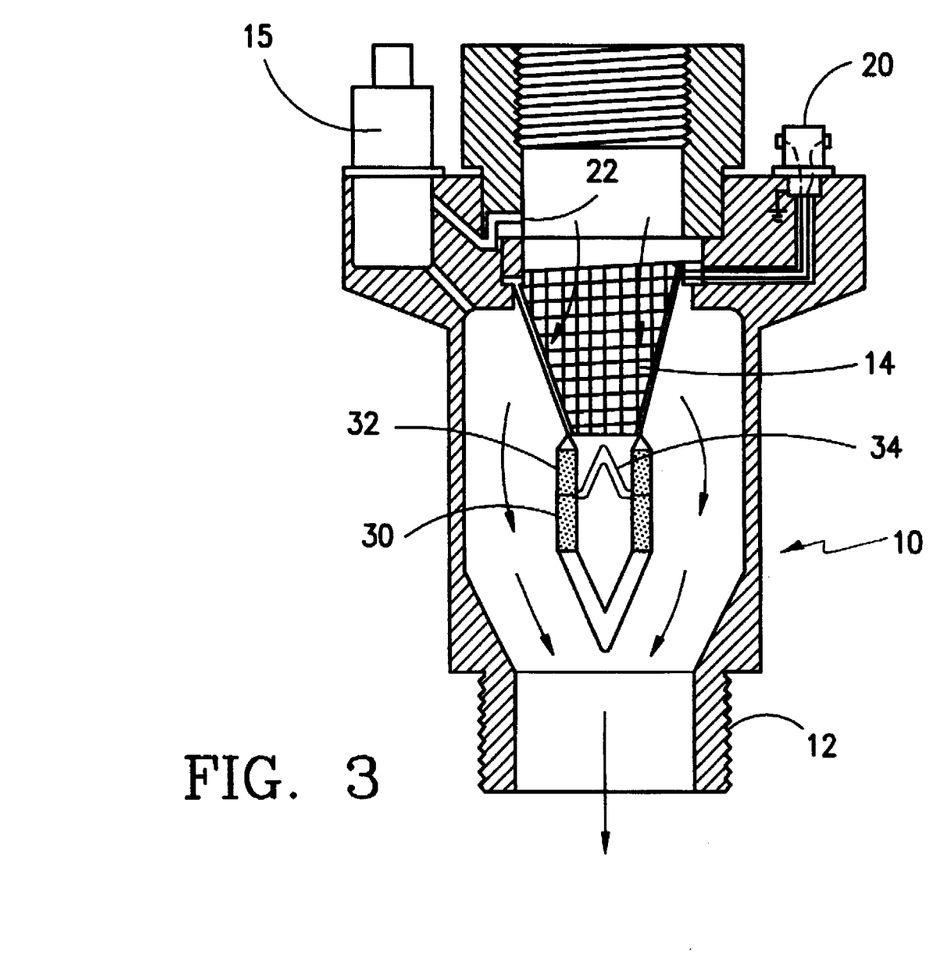
FIG. 3 is a sectional view of yet another alternate embodiment of the system.

Referring now to FIG. 3, there is shown yet another embodiment of the device. In this embodiment the conical member 34 has been placed such that its lower edge is at the junction of the two sensors 30 and 32. The location of the sensors 30 and 32 have been reversed such that the primary sensor 32 is on top and the compensating sensor 30 is on the bottom below the conical member 34. In this configuration all of the debris is collected adjacent the primary sensor 30 and the compensating sensor 32 is unaffected by the accumulated debris.

Figure 4:
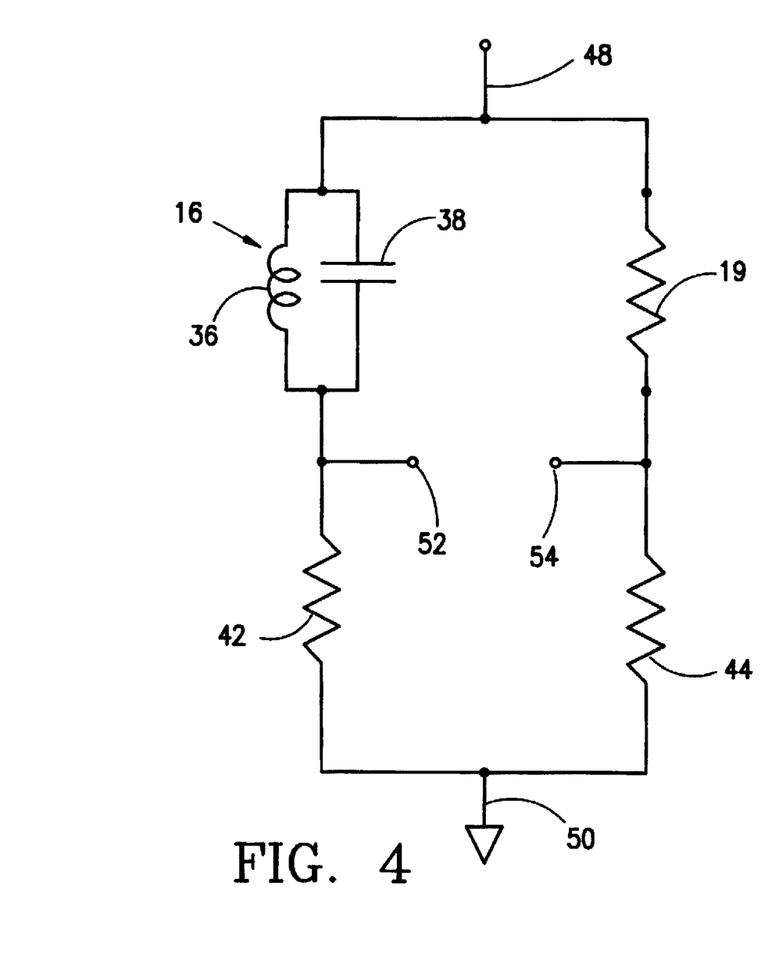
FIG. 4 is a schematic diagram of the a basic embodiment of the device using a coil with a parallel tuning capacitor and a resistor as sensors.

Referring now to FIG. 4, there is shown a schematic of a conventional bridge circuit as used in the embodiment of FIG. 1 containing a primary sensor 16 comprising inductive coil 36 and its tuning capacitor 38 connected in parallel with the coil 36 to form one leg of the bridge and a second sensor 19 which is a resistive element installed in the housing to provide temperature compensation for the bridge. To complete the resonant bridge circuit, resistors 42 and 44 are applied to the other two legs of the bridge and may be located outside of the housing of the device. The bridge is excited at input terminal 48 by a high frequency voltage whose frequency is substantially the same as the resonant frequency of the sensor 16. The bridge is connected to ground at terminal 50. The output of the bridge is then measured across terminals 52 and 54 in a conventional manner.

Figure 5:
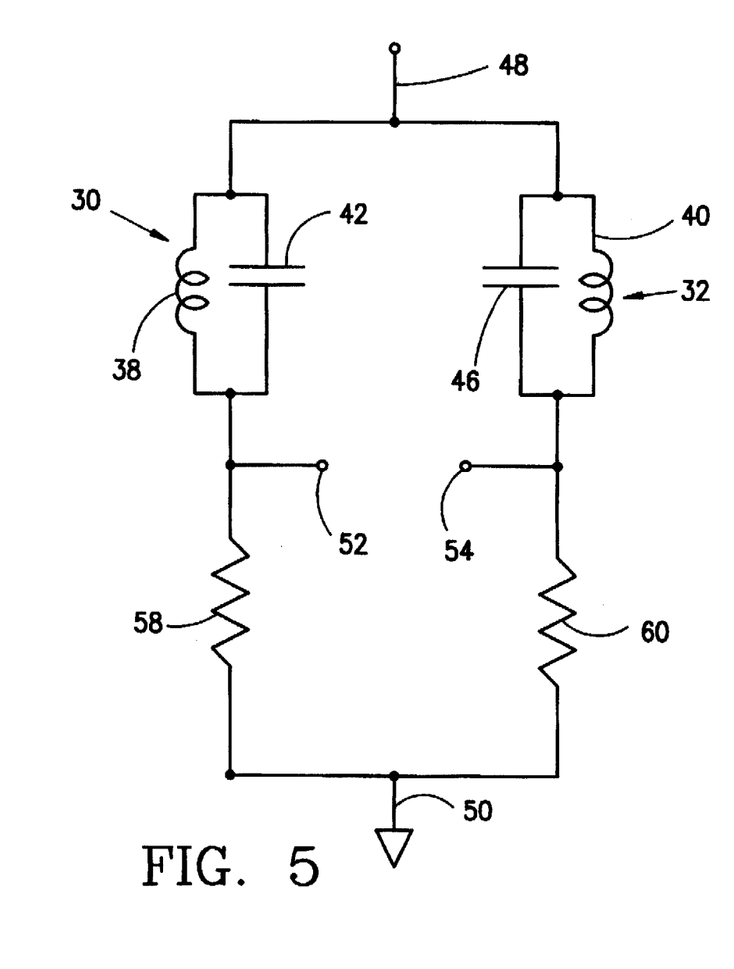
FIG. 5 is an alternate embodiment of the device utilizing two coils tuned with parallel capacitors as sensors in the bridge circuit.

Turning now to FIG. 5, the device may be assembled using a two sensors 30 and 32, each having an inductive coils 38 and 40 respectfully and parallel tuning capacitors 42 and 46 to provide two legs of the bridge circuit. In order to complete the bridge using dual inductive sensors, resistors 58 and 60 are connected to complete the conventional bridge circuit. As described in connection with the description of the sensor 16 in FIG. 4, the sensors 30 and 32 are tuned by means of the capacitors 40 and 42 to the same resonant frequency and the bridge circuit is excited at that frequency at terminals 48 and 50 in a conventional manner.

Figure 6:
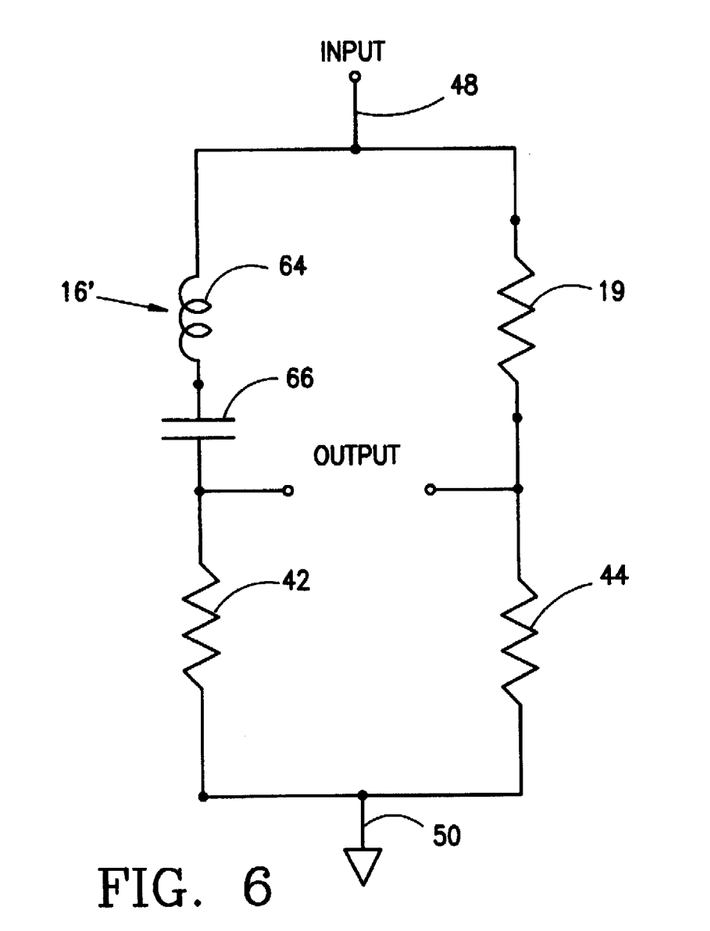
FIG. 6 is a schematic of an alternate embodiment of the device using a series capacitor for tuning the sensor coil and a resistor sensor.

Referring now to FIG. 6, there is shown an embodiment of the invention as an alternate to the embodiment of FIG. 4. In this embodiment, the primary sensor 16' is formed with an inductive coil 64 and a capacitor element 66 connected in series with the coil 64 rather than in parallel as shown in the embodiment of FIG. 4. The remainder of the circuit is substantially the same as that of FIG. 4.

Figure 7:
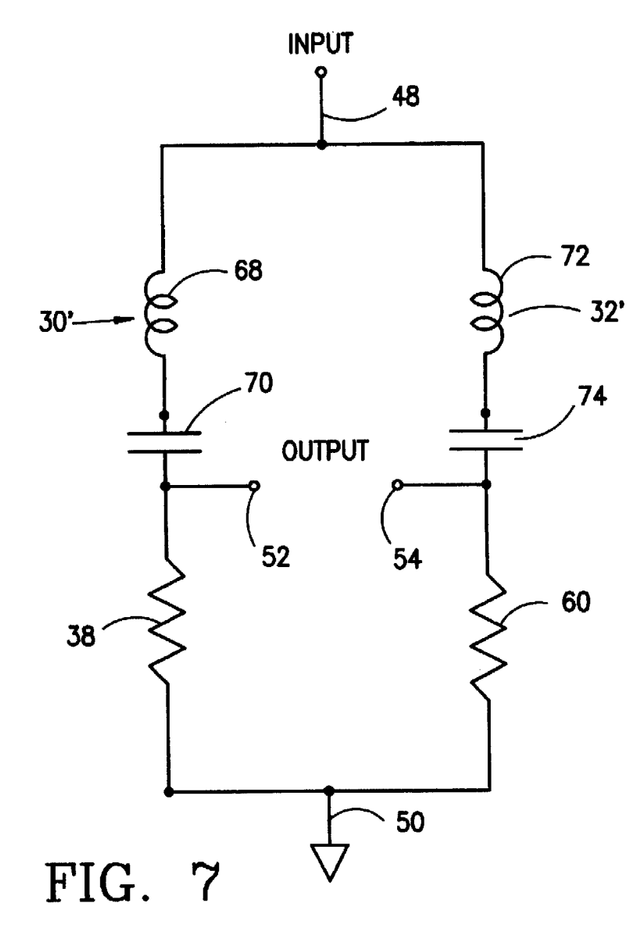
FIG. 7 is an alternate embodiment of the device utilizing two coils tuned with series resistors as sensors in the bridge circuit.

Referring now to FIG. 7, there is shown another embodiment of the invention in which there is provided a primary sensor 30' comprised of an inductive coil 68 and a series tuning capacitor 70 similar to sensor 16' of FIG. 6. The compensating sensor 32' is similar to the primary sensor 30' in that it is also comprised of an inductive coil 72 and a series tuning capacitor 74. The remaining component legs of the bridge are resistors 58 and 60. The bridge is excited at terminal 48 with ground terminal 50 as described in FIGS. 3–6. Again, the sensor coils are tuned to the same resonant frequency and the bridge circuit is excited at that same frequency.

Whether the sensor coil is tuned using a parallel or series resistor will depend upon the application. Each application is different depending on the type, size and amount of debris to be detected and identified. Connecting the components of the measuring means in a bridge circuit is required in order to provide temperature compensation for the device. Since the inductive sensors must operate in the fluid of the monitored system, and since temperature changes alter the inductance of the coil itself, it is necessary to compensate the circuit for the changes in temperature during the operation of the device.

It has been determined by experimental information that exciting the bridge with a frequency voltage at or near the resonant frequency of the inductive coil of the primary sensor increases the sensitivity of the total measuring system. The frequency of the excitation voltage is selected according to the specific debris material type to be detected. An example of this feature is demonstrated in the description of the preferred embodiment of the invention given below. In this embodiment, the frequency selected as the resonant frequency of the sensor and the excitation voltage of the bridge circuit is the frequency determined as optimum for detecting ferrous debris. In this embodiment of the invention, the coil of the primary sensor has an inductance of approximately 1.8 millihenrys and the tuning capacitor a value of approximately 120 picofarads which provides the sensor with a resonant frequency between 200 and 300 khz. The bridge is excited with a voltage having a frequency at or near the resonant frequency of the primary sensor with a sinusoidal wave form. Using these values, the disclosed device is capable of detecting as little as 5 milligrams of ferrous wear material introduced inside the coil of the inductor. Materials other than ferrous materials can also be sensed by the device in the same manner. For each material, optimum sensing requires a different frequency for the sensing coil bridge excitation voltage. Also, the frequency and capacitor values will vary according to the inductance value of the sensing coils. The use of dual resonant inductor coil sensors is desirable for bridge balance and for configuration options. Such options can increase debris capacity as shown in FIG. 2.

Referring now to FIGS. 8a–8d, there is shown the means of providing the device of this invention with the ability so operate at a plurality of frequencies for optimizing the sensing of several different materials which will allow the operator to construct a composite picture of the type and source of the debris in the system.

Figure 8A:
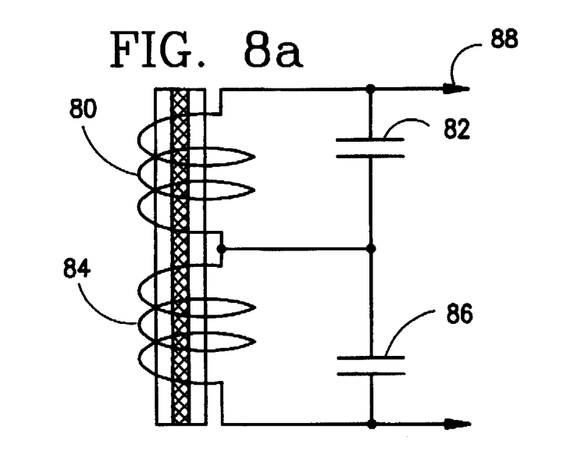
FIGS. 8a–8d describe alternate circuits for providing a plurality of sensor frequencies according to the debris to be sensed.

In the embodiment of FIG. 8a, the sensor portion of the device is made up of two separate inductive coils and their associated tuning components. One coil 80 is provided with tuning capacitor 82 and this combination has a first resonant frequency. The second coil 84 is connected with a tuning capacitor 86 to form a sensor having a second resonant frequency. The sensor is connected to the bridge across terminals 88 and 90 and can be excited at either the first resonant frequency or the second resonant frequency. By using external switching to allow bridge excitation at different frequencies, the sensors can scan the fluid in the system in this illustration for at least two different components of the debris.

Figure 8B:
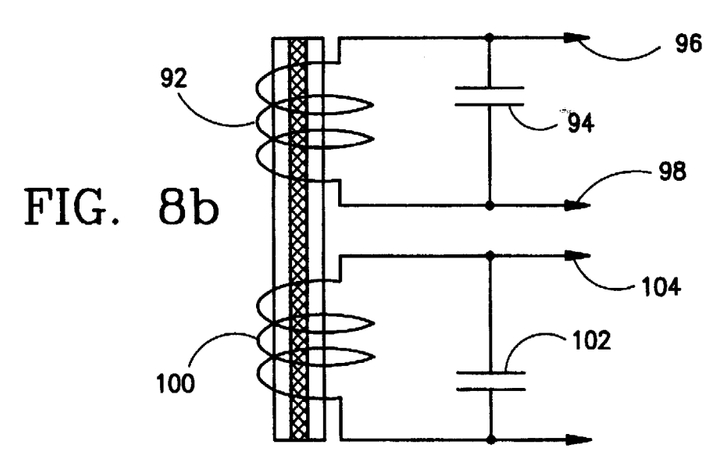

Referring now to FIG. 8b, another embodiment of the invention is described. In this circuit, as in the circuit of FIG. 8a, at least two sensor coils, 92 and 100 are provided in two separate sensor assemblies. In this embodiment, sensor coil 92 and its parallel capacitor 94 are connected to the bridge circuit shown in FIG. 4 at terminals 96 and 98. Sensor coil 100 and its parallel tuning capacitor 102 are connected to the bridge at terminals 104 and 106. These terminals 96,98,104 and 106 are brought outside of the sensing apparatus to a switching circuit so that the individual sensor coils can be excited at different resonant frequencies each of which is characteristic of a particular type of material in the debris.

Figure 8C:
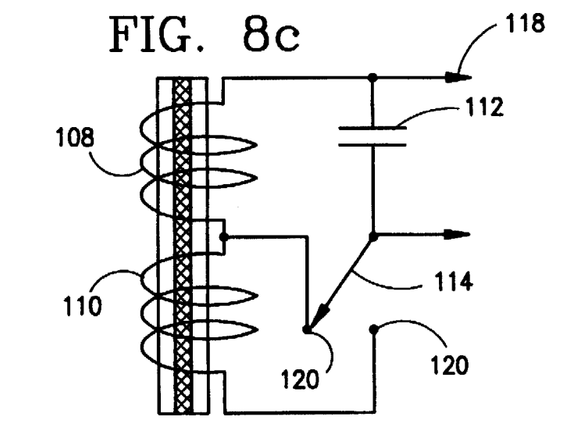

Referring now to FIG. 8c, yet another embodiment of the invention is shown. In this embodiment, the sensing coil is divided into two sections shown at 108 and 110. A single tuning capacitor 112 is connected to one end of the coil 108 and the other end is connected to switch 114. When switch 114 is connected to terminal 120, only portion 108 of the sensing coil is connecter to the bridge at terminals 116 and 118. When the switch 114 connected to terminal 122, coils 108 and 110 are connected in series to the bridge circuit terminals 108 and 110 to form a sensor having a different resonant frequency than that obtained when only portion 108 of the sensor coil is in the circuit.

Figure 8D:
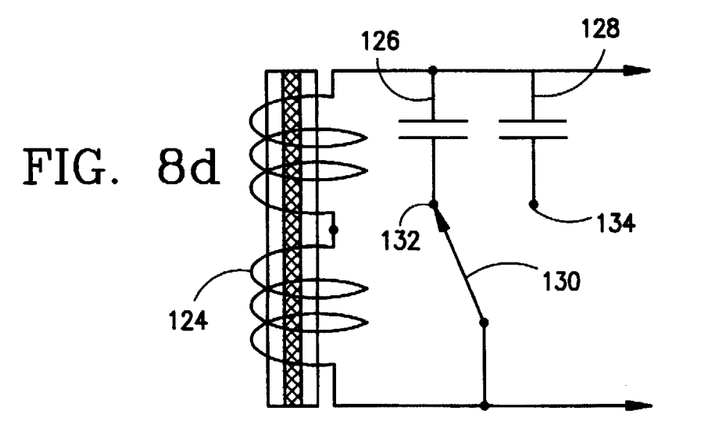

In FIG. 8d, yet another embodiment of the invention is shown. In this circuit, a single sensing coil 124 is provided. However, two capacitors 126 and 128 of different values are included in the circuit. One end of each these capacitors is connected to one end of the coil 124. The other end of these capacitors, shown at terminals 132 and 134 are connected to switch 130 which is external to the sensing assembly. When switch 130 is connected to terminal 132, capacitor 126 is connected in parallel with the coil 124 to create a circuit having a first resonant frequency. When the switch is connected to terminal 134, capacitor 128 is connected in parallel to coil 124 to form a circuit having a different resonant frequency than that using capacitor 126. Thus by switching capacitors of different value in the sensing circuit, the device can be tuned to frequencies optimum for sensing a specific component of the debris in the fluid.

Figure 9:
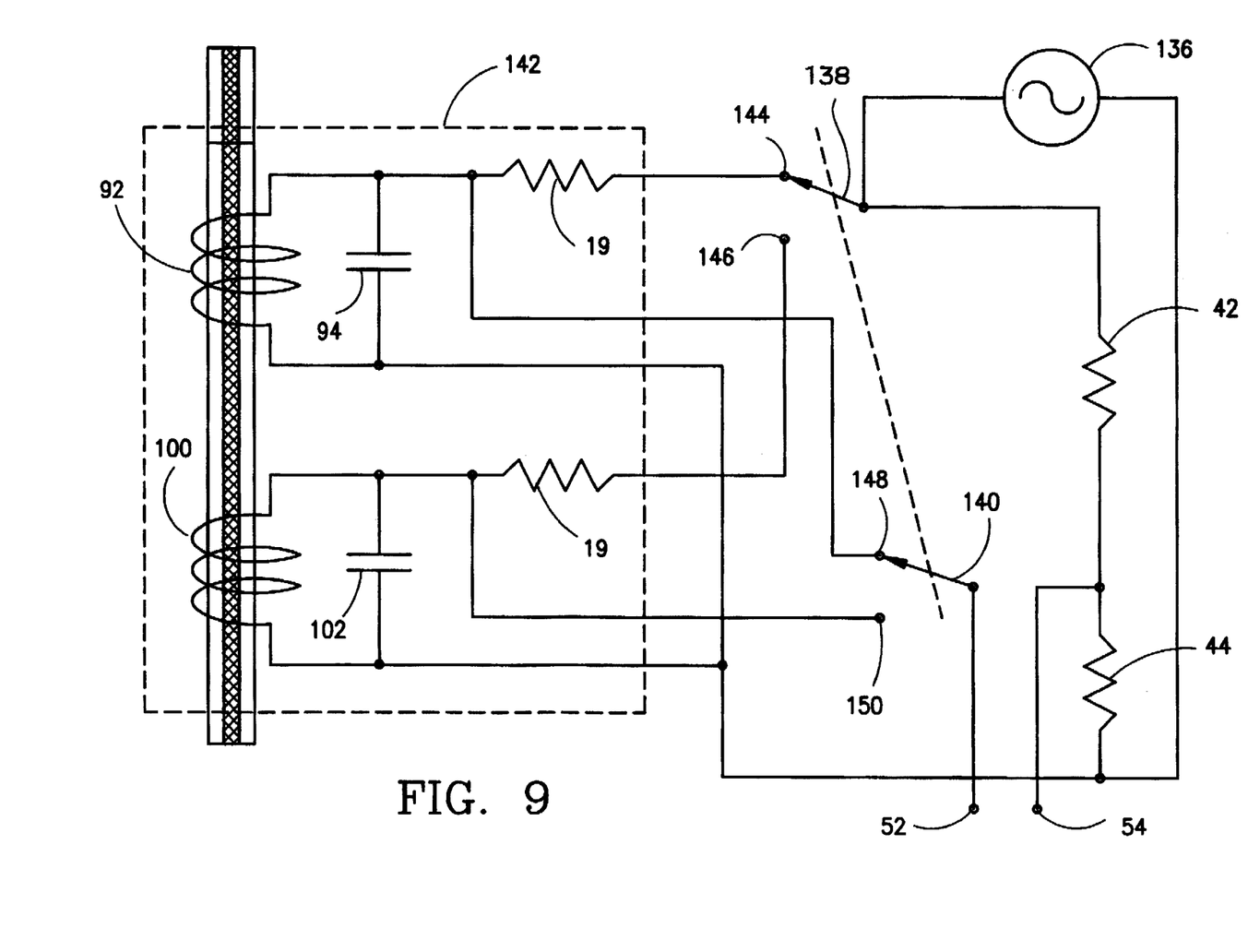
FIG. 9 is a schematic diagram of a typical switching circuit of the device.

FIG. 9 illustrates how the circuits of FIGS. 8a–8d are connected to their respective external switching means. In this example, the circuit of FIG. 8b is illustrated. Switching for circuits 8a, 8c and 8d is accomplished in a similar manner which is known to those having skill in the art. In this FIG. 9, sensing coils 92 and 100, their respective tuning capacitors 94 and 102 as well as the temperature compensating resistor 19 are all located in the sensor assembly which is placed in the fluid system to be monitored. The remaining portion of the bridge circuit, resistors 42 and 44 as well as a variable frequency power source shown at 136 are all located outside of the fluid system as are switches 138, 140 and 142 which are required to select the appropriate sensor assembly for the particular debris component to be detected.

Thus, it can be seen that there is provided by this invention a debris measuring device with high sensitivity which can, using conventional electronic means and periodic sampling with time, measure the rate of accumulation of debris, the presence of a large amount of debris and more importantly, can be externally adjusted to selectively scan the fluid system for specific components of the debris to give the operator sufficient information to evaluate the overall health of the fluid system and the apparatus operating in the fluid.

What is claimed is:

1. An apparatus for identifying, sensing the presence of and measuring the incremental changes in the amount of debris in a fluid system said apparatus comprising:

a bridge circuit for measuring said debris, said bridge circuit comprising four legs;

a housing having an internal fluid cavity and inlet and outlet openings for conducting fluid through the housing cavity;

a first sensing element formed as an inductive coil and assembled in said housing cavity;

first tuning means connected to said first sensing element in said fluid cavity for tuning said first sensing element to a preselected resonant frequency, said first sensing element and said first tuning means comprising a first sensor;

a second sensing element formed as an inductive coil and assembled in said housing cavity;

second tuning means connected to said second sensing element in said fluid cavity for tuning said second sensing element to a preselected resonant frequency, said second sensing element and said second tuning means comprising a second sensor;

switching means external to said fluids housing for selectively connecting one of said sensors as one leg of said bridge circuit;

first, second and third bridge elements, at least two of said elements being assembled external to said fluid housing, each of said bridge elements forming a separate leg of said bridge; and variable frequency power supply means for selectively exciting said bridge circuit at the resonant frequency of the sensor connected to the bridge by said switching means, the frequency of excitation of said bridge is characteristic of one type of said debris.

2. The claim according to claim 1 wherein one of said bridge elements is assembled in said fluid housing and supplies temperature compensation for the sensor connected to the bridge by said switching means.

3. The apparatus according to claim 1 wherein said first, second and third bridge elements are resistive elements.

4. The apparatus according to claim 1 wherein said first and second tuning means are connected in series with said first and second sensing elements respectively.

5. The apparatus according to claim 1 wherein said first and second tuning means are connected in parallel with said first and second sensing elements respectively.

6. The apparatus according to claim 1 wherein one of said first and second tuning means is connected in parallel with its respective sensing element and the other of said first and second tuning means is connected in series with its respective sensing element.

7. An apparatus for identifying, sensing the presence of and measuring the incremental changes in the amount of metallic debris in a fluid system said apparatus comprising:

a bridge circuit for measuring said debris, said bridge circuit comprising four legs;

a housing having an internal fluid cavity and inlet and outlet openings for conducting fluid through the housing cavity;

an inductive coil assembled in the fluid cavity of said housing, said inductive coil being divided into two sensing elements by an intermediate connection;

first tuning means assembled in said fluid cavity and connected to said first coil sensing element and said intermediate connection for tuning said first sensing element to a preselected resonant frequency, said first sensing element and said first tuning means comprising a first sensor;

second tuning means assembled in said fluid cavity and connected to said second sensing element and said intermediate connection for tuning said first sensing element to a preselected resonant frequency, said second sensing element and said second tuning means comprising a second sensor;

switching means external to said fluid housing for selectively connecting one of said sensors as one leg of said bridge circuit;

first, second and third bridge elements, at least two of said elements being assembled external to said fluid housing, each of said bridge elements forming a separate leg of said bridge; and variable frequency power supply means for selectively exciting said bridge circuit at the resonant frequency one of said sensors, said resonant frequency being characteristic of one type of said debris.

8. The apparatus according to claim 7 wherein one of said bridge elements is assembled in said fluid housing to provide temperature compensation for said bridge.

9. The apparatus according to claim 8 wherein the bridge element assembled in said fluid cavity is a resistive element.

10. The apparatus according to claim 8 wherein said first and second tuning means are capacitors.

11. An apparatus for identifying, sensing the presence of and measuring the incremental changes in the amount of debris in a fluid system said apparatus comprising:

a bridge circuit for measuring said debris, said bridge circuit comprising four legs;

a housing having an internal fluid cavity and inlet and outlet openings for conducting fluid through the housing cavity;

an inductive coil assembled in the fluid cavity of said housing, said inductive having first and second end connections and an intermediate connection between said first and second end connections;

tuning means assembled in said fluid cavity and connected to said first end connection of said inductive coil;

first switching means external to said housing having first and second positions for selectively switching said tuning means between said intermediate connection and said second end connection, said first switching position creating a first sensor having a first preselected resonant frequency and said second switch position creating a second sensor having a second resonant frequency;

second switching means external to said fluid housing for selectively connecting one of said sensors as one leg of said bridge circuit;

first, second and third bridge elements, at least two of said elements being assembled external to said fluid housing, each of said bridge elements forming a separate leg of said bridge; and variable frequency power supply means for selectively exciting said bridge circuit at the resonant frequency one of said sensors, said resonant frequency being characteristic of one type of said debris.

12. The apparatus according to claim 11 wherein one of said bridge elements is assembled in said fluid housing to provide temperature compensation for said bridge.

13. The apparatus according to claim 12 wherein the bridge element assembled in said fluid cavity is a resistive element.

14. The apparatus according to claim 11 wherein said tuning means is a capacitor.

15. An apparatus for identifying, sensing the presence of and measuring the incremental changes in the amount of debris in a fluid system said apparatus comprising:

a bridge circuit for measuring said debris, said bridge circuit comprising four legs;

a housing having an internal fluid cavity and inlet and outlet openings for conducting fluid through the housing cavity;

an inductive coil assembled in the fluid cavity of said housing, said inductive having first and second end connections;

first tuning means assembled in said fluid cavity and connected to said first end connection of said inductive coil;

second tuning means connected to said first end connection of said inductive coil;

first switching means external to said housing having first and second positions for selectively connecting said first tuning means and said second tuning means to said second end connection, said first switching position creating a first sensor having a first preselected resonant frequency and said second switch position creating a second sensor having a second resonant frequency;

second switching means external to said fluid housing for selectively connecting one of said sensors as one leg of said bridge circuit;

first, second and third bridge elements, at least two of said elements being assembled external to said fluid housing, each of said bridge elements forming a separate leg of said bridge; and variable frequency power supply means for selectively exciting said bridge circuit at the resonant frequency of one of said sensors, said resonant frequency being characteristic of one type of said debris.

16. The apparatus according to claim 15 wherein one of said bridge elements is assembled in said fluid housing to provide temperature compensation for said bridge.

17. The apparatus according to claim 16 wherein the bridge element assembled in said fluid cavity is a resistive element.

18. The apparatus according to claim 16 wherein said first and second tuning means are capacitors.

19. An apparatus for identifying, sensing the presence of and measuring the incremental changes in the amount of debris in a fluid system said apparatus comprising:

a bridge circuit for measuring said debris, said bridge circuit comprising four legs;

a housing having an internal fluid cavity and inlet and outlet openings for conducting fluid through the housing cavity;

a plurality of sensors assembled in said fluid cavity, each of said sensors comprising an inductive coil and a tuning means, said tuning means being selected to give its respective sensor a preselected resonant frequency, each of said frequencies being characteristic of one type of said debris;

switching means external to said housing for connecting one of said sensors as one leg of said bridge; and Variable frequency power supply means for exciting said bridge at the resonant frequency of one of said sensors.

20. The apparatus according to claim 19 wherein said tuning means are capacitors.

21. The apparatus according to claim 20 wherein each of said capacitors is connected in parallel with its respective inductive coil.

22. The apparatus according to claim 20 and further comprising a screen member mounted in the fluid cavity between the inlet and outlet openings, such that the fluid flows through the screen between the inlet and outlet openings, said plurality of sensors assembled in said housing to surround a portion of said screen.

23. The apparatus according to claim 19 wherein said tuning means are capacitors.

24. The apparatus according to claim 23 wherein each of said capacitors is connected in parallel with its respective inductive coil.

* * * * *

UNITED STATES PATENT AND TRADEMARK OFFICE
CERTIFICATE OF CORRECTION

PATENT NO. : 5,663,642
DATED : September 2, 1997
INVENTOR(S) : William E. Rumberger et al It is certified that error appears in the above-indentified patent and that said Letters Patent is hereby corrected as shown below:

Claim 1, column 6, line 54, "fluids" should be --fluid--.

Claim 7, column 7, line 49, before "one" insert --of--.

Claim 11, column 7, line 67, between "inductive" and "having" insert --coil--; and        column 8, line 23, before "one" insert --of--.

Claim 15, column 8, line 42, between "inductive" and "having" insert --coil--.

Signed and Sealed this

Seventeenth Day of February, 1998

*Attest:*

BRUCE LEHMAN

*Attesting Officer*     *Commissioner of Patents and Trademarks*